United States Patent
Cates

(10) Patent No.: US 7,123,959 B2
(45) Date of Patent: Oct. 17, 2006

(54) METHOD AND APPARATUS FOR PREVENTING CARDIAC ARRHYTHMIAS WITH ENDOVASCULAR STIMULATION

(75) Inventor: Adam W. Cates, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 571 days.

(21) Appl. No.: 10/105,941

(22) Filed: Mar. 25, 2002

(65) Prior Publication Data

US 2003/0181951 A1 Sep. 25, 2003

(51) Int. Cl.
*A61N 1/18* (2006.01)
(52) U.S. Cl. .......................................... 607/9
(58) Field of Classification Search ............... 607/4–5, 607/9, 14, 17, 25
See application file for complete search history.

(56) References Cited

U.S. PATENT DOCUMENTS

| 5,411,531 A | 5/1995 | Hill et al. ................. 607/14 |
| 5,419,338 A | 5/1995 | Sarma et al. .............. 128/703 |
| 5,522,854 A | 6/1996 | Ideker et al. ................ 607/6 |
| 5,578,061 A | 11/1996 | Stroetmann et al. .......... 607/4 |
| 5,645,570 A | 7/1997 | Corbucci ..................... 607/5 |
| 5,700,282 A | 12/1997 | Zabara ........................ 607/9 |
| 6,035,233 A | 3/2000 | Schroeppel et al. ........ 600/515 |
| 6,144,878 A | 11/2000 | Schroeppel et al. ........ 600/515 |
| 6,292,695 B1 | 9/2001 | Webster, Jr. et al. ......... 607/14 |
| 6,622,041 B1 * | 9/2003 | Terry et al. .................. 607/9 |

OTHER PUBLICATIONS

Hasdemir, C.,et al. ,"Endovascular Stimulation of Autonomic Neural Elements in the Superior Vena Cava Using a Flexible Loop Catheter", *Pacing and Clinical Electrophysiology*, v.24, Part II, (Apr. 2000),691.

Schauerte, P.,et al. , "Transvenous Parasympathetic Nerve Stimulation in the Inferior Vena Cava and Atrioventricular Conduction", *J. Cardiovasc. Electrophysiol.*, 11 (1), (Jan. 2000),64-69.

Schauerte, P..,et al. ,"Ventricular Rate Control During Atrial Fibrillation by Cardiac Parasympathetic Nerve Stimulation: A Transvenous Approach", *J. Am. Coll. Cardiol.*, 34 (7), (Dec. 1999),2043-2050.

Scherlag, M.A. ,et al. ,"Endovascular Neural Stimulation Via a Novel Basket Electrode Catheter: Comparison of Electrode Configurations", *J. Interv. Card Electrophysiol*, 4 (1), (Apr. 2000),219-224.

* cited by examiner

*Primary Examiner*—Mark Bockelman
(74) *Attorney, Agent, or Firm*—Schwegman, Lundberg, Woessner, & Kluth, P.A.

(57) ABSTRACT

Certain cardiac arrhythmias can be prevented by appropriate electrical stimulation of autonomic nerves innervating the heart. An implantable cardiac rhythm management device is configured to deliver such stimulation when an autonomic imbalance is predicted to be present via an endovascular electrode. Autonomic imbalance may be predicted to be present based upon circadian rhythms, detected heart rates, or detected heart rate variability.

9 Claims, 2 Drawing Sheets

METHOD AND APPARATUS FOR PREVENTING CARDIAC ARRHYTHMIAS WITH ENDOVASCULAR STIMULATION

FIELD OF THE INVENTION

This invention pertains to methods and apparatus for the management of cardiac rhythm disorders.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include sinus tachycardia, ventricular tachycardia, ventricular fibrillation (VF), atrial tachycardia, and atrial fibrillation (AF). Tachyarrhythmias can be due to abnormal excitation by normal pacemaker tissue, an ectopic excitatory focus, or a re-entry phenomenon. Tachycardia occurs when the heart contracts relatively normally but at a rapid rate, while fibrillation occurs when the chamber depolarizes in a chaotic fashion with abnormal depolarization waveforms as reflected by an EKG.

An electrical defibrillation shock applied to a heart chamber can be used to terminate most tachyarrhythmias by depolarizing excitable myocardium and rendering it refractory. Implantable cardioverter/defibrillators (ICDs) provide this kind of therapy by delivering a shock pulse to the heart when fibrillation is detected by the device. ICDs can be designed to treat either atrial or ventricular tachyarrhythmias, or both, and may also incorporate cardiac pacing functionality. The most dangerous tachyarrhythmias are ventricular tachycardia and ventricular fibrillation, and ICDs have most commonly been applied in the treatment of those conditions. Another type of electrical therapy for tachycardia is antitachycardia pacing (ATP). In ATP, the heart is competitively paced with one or more pacing pulses in an effort to interrupt the reentrant circuit causing the tachycardia. Modem ICD's usually have ATP capability so that ATP therapy is delivered to the heart when a tachycardia is detected, while a shock pulse is delivered when fibrillation occurs.

ICDs are also capable of detecting atrial tachyarrhythmias, such as atrial fibrillation and atrial flutter, and delivering a shock pulse to the atria in order to terminate the arrhythmia. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy.

As described above, an implantable device may deliver appropriate therapy to terminate certain detected arrhythmias. Such therapies are not invariably successful, however, and, even when they are, may require repeated application until the arrhythmia is finally terminated. Defibrillation shocks also subject the patient to some discomfort. It would be more beneficial if an implantable device could detect when a pre-arrhythmic condition exists and deliver electro-stimulatory therapy in a manner that prevents the arrhythmia from occurring in the first instance.

SUMMARY OF THE INVENTION

The present invention relates to an implantable cardiac rhythm management device having an autonomic stimulation channel for electrically stimulating sympathetic or parasympathetic nerves in order to prevent the onset of arrhythmias in susceptible patients. In those patients, increased relative activity of either sympathetic or parasympathetic nerves acting on the heart can be responsible for triggering the onset of arrhythmic episodes. In accordance with the invention, stimulation of either sympathetic or parasympathetic nerves innervating the heart can be used to restore autonomic balance and prevent such triggered episodes. The autonomic stimulation channel includes a pulse generator and an endovascular electrode for stimulating nerves that lie adjacent a blood vessel within which the electrode is disposed. The device may be configured to deliver such autonomic stimulation when an autonomic imbalance is detected by monitoring heart rate or heart rate variability. Autonomic stimulation may also be delivered at timed intervals when autonomic imbalance is predicted to be present according to circadian rhythms.

DETAILED DESCRIPTION

Figure 1:
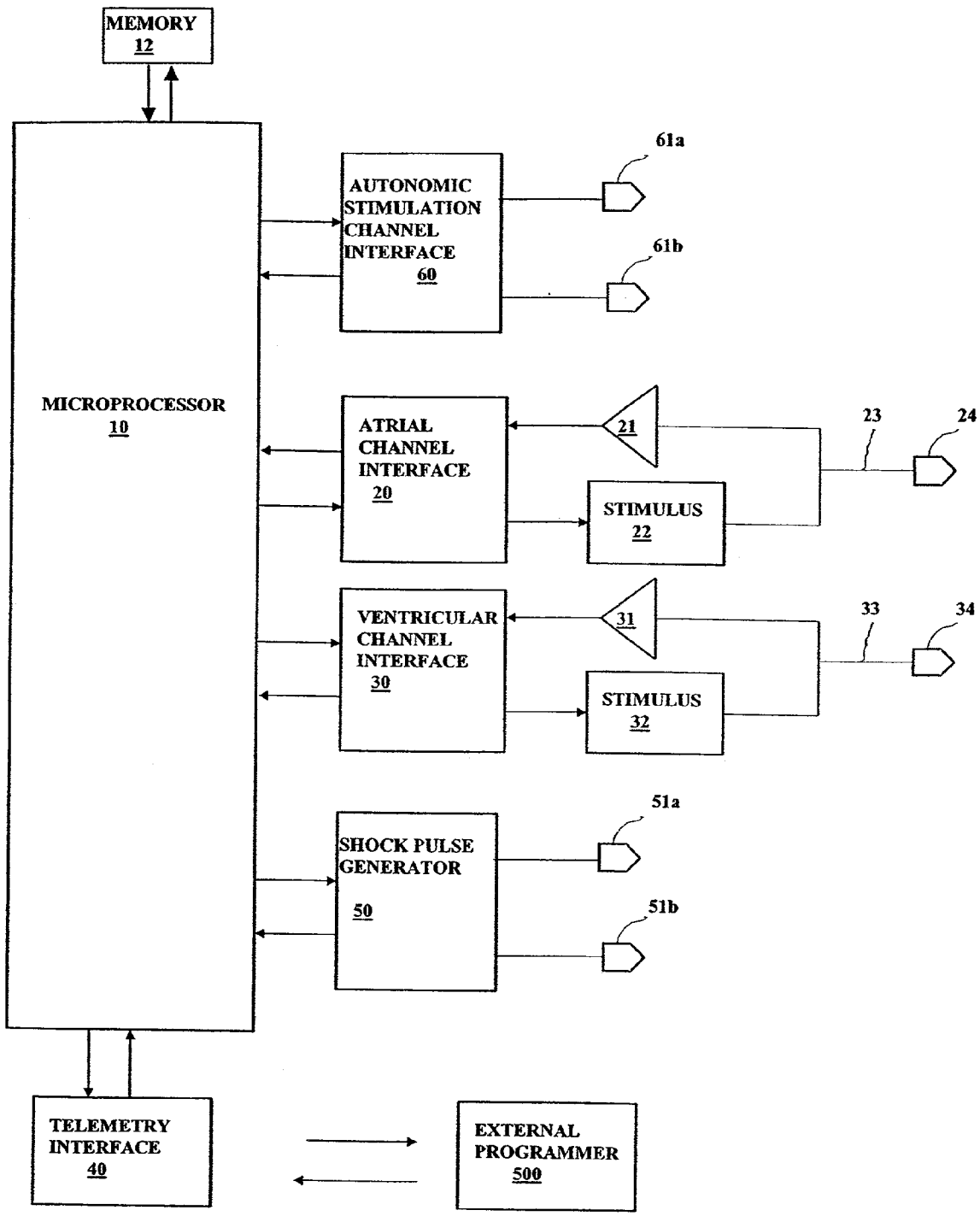
FIG. 1 is a block diagram of an exemplary cardiac rhythm management device for delivering autonomic stimulation.

Autonomic imbalance may be a factor in the development of cardiac arrhythmias in some patients. Such an imbalance refers to the relative activity of the sympathetic and para-sympathetic arms of the autonomic nervous system. Sympathetic and parasympathetic nerves act on the heart via beta-adrenergic and muscarinic receptors, respectively, to affect both heart rate and the velocity at which excitation is conducted through the heart. Both of these effects may contribute to the development of arrhythmias under certain circumstances in individuals otherwise so disposed.

It is well-known, for example, that an increase in the activity of the sympathetic nervous system can make the onset of such arrhythmias more likely and may serve as a trigger for such events in certain patients. In one of its aspects, the present invention provides an implantable cardiac rhythm management device that counteracts the arrhythmogenic effects of increased sympathetic activity by electrically stimulating the parasympathetic nerves innervating the heart with an endovascular electrode. Such a device may utilize a bipolar electrode incorporated into a lead adapted for transvenous insertion, such as into the superior or inferior vena cava. In another embodiment, the bipolar electrode may be incorporated within a shock lead normally used for delivering cardioversion/defibrillation shocks to the heart. A pulse generator in the device then delivers electrical stimulation via the bipolar electrode to the inner surface of the blood vessel and stimulates the parasympathetic nerves that run adjacent thereto. The electrical stimulation may be, for example, in the form of a square-wave or truncated exponential pulse train at a frequency of between 5 and 50 Hz. The result of such electrical stimulation is a slowing of sinus rhythm due to increased parasympathetic activity acting on the sino-atrial node as well as a negative dromotropic effect (i.e., slowing of excitation conduction) on the atrio-ventricular node and the myocardium, both of which may inhibit the triggering of an arrhythmia.

In an exemplary device, a controller is programmed to cause delivery of parasympathetic stimulation when increased sympathetic activity is either detected or predicted to be present. The level of sympathetic activity may be assessed by monitoring the heart rate via a ventricular sensing channel so that increased sympathetic activity is detected when the time interval between successive ventricular senses (i.e., RR intervals) falls below a specified minimum threshold value. In another embodiment, the level of sympathetic activity is assessed by measuring the variability of the heart rate which is known to be influenced by the relative levels of sympathetic and parasympathetic activity. In still another embodiment, the controller includes a timer for delivering the parasympathetic stimulation at periodic intervals according to circadian rhythms that predict when increased sympathetic activity will be present.

Increased parasympathetic activity can also be responsible for triggering arrhythmias in certain individuals. These patients may be treated with an implantable device configured to stimulate sympathetic nerves when increased parasympathetic activity is detected or predicted to be present. Whether sympathetic or parasympathetic nerves are stimulated by an endovascular electrode depends upon its location. For example, sympathetic nerves are predominately found adjacent the anterior surface of the vena cava, while parasympathetic nerves are mostly found adjacent the posterior surface. Increased parasympathetic activity can be detected by measurement of heart rate or heart rate variability or can be predicted to be present according to circadian rhythms.

1. Exemplary Hardware Platform

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. In the description that follows, a microprocessor-based cardiac rhythm management device will be referred to as incorporating the system and method that is the present invention. In the embodiment to be described, the invention is implemented with a controller made up of a microprocessor executing programmed instructions in memory. It should be appreciated, however, that certain functions of a cardiac rhythm management device could be controlled by custom logic circuitry either in addition to or instead of a programmed microprocessor. The terms "controller" or "circuitry" as used herein should therefore be taken to encompass either custom circuitry (i.e., dedicated hardware) or a microprocessor executing programmed instructions contained in a processor-readable storage medium along with associated circuit elements.

Implantable cardiac rhythm management devices, such as pacemakers and ICD's, are electronic devices that are implanted subcutaneously on a patient's chest with leads threaded intravenously into the heart to connect the device to electrodes used for sensing electrical activity and for electrical stimulation of the heart. FIG. 1 is a system diagram of a microprocessor-based cardiac rhythm management device with the capability of delivering autonomic stimulation in response to detected or predicted autonomic imbalance as well as delivering cardioversion/defibrillation shocks and antitachycardia pacing (ATP) therapy. The device may also be configured to deliver conventional bradycardia pacing as well. The controller 10 is a microprocessor that communicates with a memory 12 via a bidirectional data bus. The memory 12 typically comprises a ROM (read-only memory) for program storage and a RAM (random-access memory) for data storage. The device has atrial and ventricular sensing/pacing channels that respectively include electrodes 24 and 34, leads 23 and 33, sensing amplifiers 21 and 31, pulse generators 22 and 32, and channel interfaces 20 and 30. Incorporated into each sensing/pacing channel is thus a pacing channel made up of the pulse generator connected to the electrode and a sensing channel made up of the sense amplifier connected to the electrode. In this embodiment, a single electrode is used for sensing and pacing in each channel, known as a unipolar lead. Other embodiments may employ bipolar leads that include two electrodes for outputting a pacing pulse and/or sensing intrinsic activity. The channel interfaces communicate bidirectionally with microprocessor 10 and include analog-to-digital converters for digitizing sensing signal inputs from the sense amplifiers and registers that can be written to by the microprocessor in order to adjust the gain and threshold values for the sensing amplifiers, output pacing pulses, and change the pacing pulse amplitude and/or duration. An autonomic stimulation channel is provided for stimulating sympathetic or parasympathetic nerves and includes a channel interface 60, a pulse generator 61, and a bipolar lead with electrodes 61a and 61b. Also provided are a shock pulse generator 50 with shock electrodes 51a and 51b and a telemetry interface 40 for communicating with an external programmer 500.

The controller 10 controls the overall operation of the device in accordance with programmed instructions stored in memory, including controlling the delivery of paces or autonomic stimulation, interpreting sense signals received from the sensing channels, and implementing timers that may be used for various purposes. The sensing circuitry of the pacemaker detects a chamber sense when an electrogram signal (i.e., a voltage sensed by an electrode representing cardiac electrical activity) generated by a particular channel exceeds a specified detection threshold. A chamber sense may be either an atrial sense or a ventricular sense depending on whether it occurs in the atrial or ventricular sensing channel. Pacing algorithms used in particular pacing modes employ such senses to trigger or inhibit pacing. By measuring the interval between successive atrial and ventricular senses, the controller is also able to measure atrial and ventricular rates and detect arrhythmias in those chambers using rate-based criteria.

2. Exemplary Delivery Scheme

Figure 2:
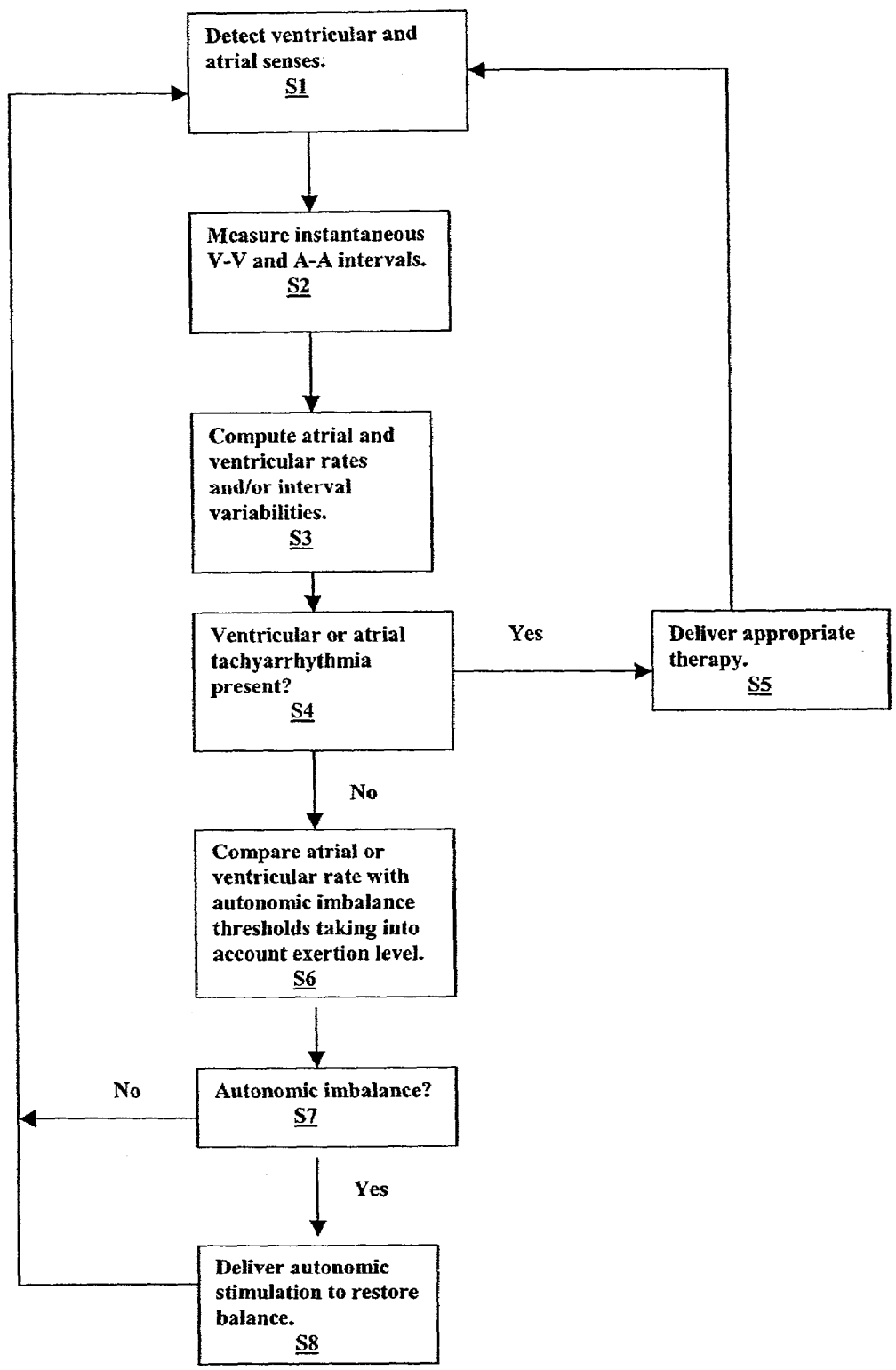
FIG. 2 illustrates an exemplary scheme for delivering autonomic stimulation.

FIG. 2 illustrates the steps involved in an exemplary scheme for delivering autonomic stimulation for arrhythmia prevention as could be implemented with code executed by the controller 10. Step S1 represents the detection of atrial and ventricular senses performed by the device in the course of its normal operation which may include bradycardia pacing as well as measurement of heart rates. Steps S2 and S3 represent computation of intrinsic rates in the atria and ventricles by measurement of the time intervals between successive senses in those chambers. Such rates may be time-averaged by appropriate filtering of the measured intervals. If a tachyarrhythmia is detected at step S4 in accordance with rate-based criteria, appropriate anti-arrhythmia therapy (e.g., anti-tachycardia pacing or a defibrillation shock) may be delivered by the device if it is configured to do so at step S5. Whether or not such therapy is delivered, the device takes no action with respect to autonomic stimulation if a tachyarrhythmia in the atria or ventricles is detected and continues monitoring heart rates as represented by steps S1 and S2. If no tachyarrhythmia is detected, the computed atrial or ventricular rate is compared with an autonomic imbalance threshold in order to ascertain whether there is relatively increased activity of the sympathetic or parasympathetic nervous system. The autonomic imbalance threshold would be an upper limit for the computed rate in order to detect increased sympathetic activity and a lower limit for detecting increased parasympathetic activity. The upper and/or lower limits making up the autonomic imbalance threshold may also be modified in accordance with a measured exertion level in order to take into account the effects on autonomic activity brought about by changing metabolic demand before an autonomic imbalance warranting intervention is declared. If such an autonomic imbalance is detected at step S7, autonomic stimulation is delivered at step S8 through the autonomic stimulation channel. Stimulation pulses at a specified frequency and for a specified time duration are output to the electrodes 61a and 61b to thereby stimulate either sympathetic or parasympathetic nerves innervating the heart and restore cardiac autonomic balance. As noted earlier, autonomic stimulation may also be delivered in another embodiment at timed intervals when autonomic imbalance is predicted to be present based upon known circadian rhythms.

In another embodiment, autonomic stimulation may be delivered when an imbalance between sympathetic and parasympathetic activity is detected based upon heart rate variability. It has been found that spectral analysis of heart rate variability can be used to determine the relative levels of sympathetic and parasympathetic activity in a subject. Heart rate variability refers to the changes in heart rate that occur during a sinus rhythm (i.e., with normally activated and conducted heartbeats) and is primarily due to the interaction of the sympathetic and parasympathetic nervous systems. Low frequency variation in heart rate is due to both parasympathetic (or vagal) and sympathetic activity, while high frequency variation is primarily due to only parasympathetic activity. The ratio of low frequency variation to high frequency variation can thus be used as an indicator of the level of autonomic balance.

As described above, a cardiac rhythm management device can be programmed to measure and collect the time intervals between successive ventricular senses, referred to as RR intervals, for a period of time or a specified number of beats. The resulting series of RR interval values can then be stored as a discrete signal and either used directly as indexed by heartbeat or resampled at a specified sampling frequency in order to equalize the time intervals. The RR interval signal can then be analyzed to determine its energies in defined high and low frequency bands. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity, for example. Although spectral analysis of an RR interval signal can be performed directly in the frequency domain, a time-domain technique for determining the signal power in defined high and low frequency bands is preferably used for reasons of computational economy.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An implantable cardiac rhythm management device, comprising:
    a ventricular sensing channel;
    an autonomic stimulation channel including a pulse generator and a stimulation electrode adapted for endovascular disposition adjacent sympathetic nerves innervating the head;
    a controller programmed to predict the presence of an autonomic imbalance due to increased parasympathetic activity by measurement of heart rate via the ventricular sensing channel; and,
    wherein the controller is further programmed to cause the delivery of autonomic stimulation pulses for stimulating sympathetic nerves when an autonomic imbalance reflecting increased parasympathetic activity is predicted to be present.

2. The device of claim 1 wherein the autonomic stimulation channel includes a bipolar stimulation electrode incorporated into a lead adapted for intravenous insertion.

3. The device of claim 1 further comprising a cardioversion/defibrillation shocking channel that includes a shock pulse generator and a shock lead, and wherein the autonomic stimulation channel includes a bipolar stimulation electrode incorporated into the shock lead.

4. The device of claim 1 wherein the pulse generator delivers autonomic stimulation in the form of a pulse train.

5. The device of claim 4 wherein the pulse train is at a frequency of between 5 and 50 Hz.

6. The device of claim 1 wherein the controller is programmed to monitor heart rate via the ventricular sensing channel and to detect increased parasympathetic activity based on the time intervals between successive ventricular senses.

7. The device of claim 6 wherein increased parasympathetic activity is detected based on an average of RR intervals taken over a specified period of time.

8. The device of claim 1 wherein the controller is programmed to monitor heart rate via the ventricular sensing channel and to detect increased parasympathetic activity based upon the variability of the measured heart rate.

9. The device of claim 1 wherein the controller is programmed to deliver sympathetic stimulation at periodic time intervals when increased parasympathetic activity is predicted to be present based upon circadian rhythms.

* * * * *

UNITED STATES PATENT AND TRADEMARK OFFICE
CERTIFICATE OF CORRECTION

| | | |
|---|---|---|
| PATENT NO. | : 7,123,959 B2 | Page 1 of 1 |
| APPLICATION NO. | : 10/105941 | |
| DATED | : October 17, 2006 | |
| INVENTOR(S) | : Cates | |

It is certified that error appears in the above-identified patent and that said Letters Patent is hereby corrected as shown below:

In column 6, line 21, in Claim 1, delete "head;" and insert -- heart; --, therefor.

Signed and Sealed this

Sixteenth Day of January, 2007

JON W. DUDAS
*Director of the United States Patent and Trademark Office*